(12) United States Patent
Lal et al.

(10) Patent No.: US 9,512,077 B2
(45) Date of Patent: Dec. 6, 2016

(54) PROCESS FOR THE PREPARATION OF METHYLPHENIDATE HYDROCHLORIDE AND ITS INTERMEDIATES THEREOF

(71) Applicant: ZCL CHEMICALS LTD., Mumbai (IN)

(72) Inventors: Agarwal Nand Lal, Gujarat (IN); Chandrashekhar Singh, Gujarat (IN); Mubashshir Ahmed, Gujarat (IN); Bhavsar Rahul Arunbhai, Gujarat (IN)

(73) Assignee: ZCL CHEMICALS LTD., Mumbai, Maharashtra (IN)

( * ) Notice: Subject to any disclaimer, the term of this patent is extended or adjusted under 35 U.S.C. 154(b) by 0 days.

(21) Appl. No.: 14/339,460

(22) Filed: Jul. 24, 2014

(65) Prior Publication Data

US 2015/0051400 A1 Feb. 19, 2015

(30) Foreign Application Priority Data

Aug. 14, 2013 (IN) .......................... 2676/MUM/2013

(51) Int. Cl.
*C07D 211/32* (2006.01)
*C07D 211/34* (2006.01)

(52) U.S. Cl.
CPC ................... *C07D 211/34* (2013.01)

(58) Field of Classification Search
CPC .................................................... C07D 211/32
USPC ................................................. 546/229, 233
See application file for complete search history.

(56) References Cited

U.S. PATENT DOCUMENTS

| | | | | |
|---|---|---|---|---|
| 2,838,519 A | * | 6/1958 | Rometsch | 546/238 |
| 6,100,401 A | * | 8/2000 | Prashad et al. | 546/233 |
| 7,247,730 B2 | * | 7/2007 | Gutman | C07D 211/34 546/183 |
| 7,459,467 B2 | * | 12/2008 | Kumar et al. | 546/233 |
| 7,459,560 B2 | * | 12/2008 | Khetani et al. | 546/233 |

FOREIGN PATENT DOCUMENTS

WO WO2011/677783 * 6/2011

OTHER PUBLICATIONS

Dalby et al. "One-pot synthesis . . . " Handbook Chiral Chem. pp. 419-428 (2005).*
Enantioselective synthesis, Wikipedia p. 1-10 (2016).*

* cited by examiner

*Primary Examiner* — Celia Chang
(74) *Attorney, Agent, or Firm* — Prakash Nama; Global IP Services, PLLC

(57) ABSTRACT

The present invention relates to an industrially feasible and economically viable process for the preparation of methylphenidate hydrochloride of formula I and its intermediates thereof.

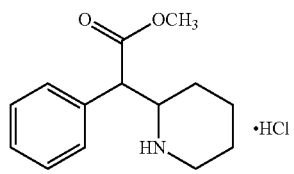

Formula I

6 Claims, No Drawings

PROCESS FOR THE PREPARATION OF METHYLPHENIDATE HYDROCHLORIDE AND ITS INTERMEDIATES THEREOF

FIELD OF THE INVENTION

The present invention relates to an industrially applicable process for the preparation of methylphenidate hydrochloride of formula I,

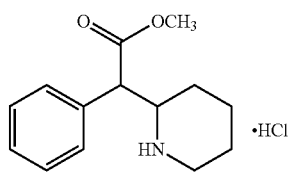

Formula I

BACKGROUND OF THE INVENTION

Methylphenidate (Ritalin) is a psychostimulant drug approved for treatment of ADHD or attention-deficit hyperactivity disorder, postural orthostatic tachycardia syndrome and narcolepsy. It was first licensed by the FDA in 1955 for treating ADHD, prescribed from 1960, and became heavily prescribed in the 1990s, when the diagnosis of ADHD itself became more widely accepted. It is available worldwide with different brand names like Concerta®, Daytrana®, Metadate CD®, Metadate® ER, Methylin®, Quillivant™ XR, Ritalin LA®, Ritalin-SR®, Ritalin®. Here 2-phenyl-2-(piperidin-2-yl) acetamide is key intermediate to prepare methylphenidate or its salts thereof.

Methylphenidate       2-phenyl-2-(piperidin-2-yl) acetamide

Until the introduction of d-threo methylphenidate hydrochloride, dexmethylphenidate hydrochloride, Focalin®) in 2002, all marketed forms of methylphenidate contained a 50:50 racemic mixture of d-threo methylphenidate and l-threo methylphenidate in the form of the hydrochloride salt. In 2007, a transdermal patch containing racemic dl-threo methylphenidate (Daytrana®) was approved by the FDA.

U.S. Pat. No. 2,957,880 describes a sequence involving the resolution of the amide derivative of the corresponding erythro isomer, conversion to the threo isomer, followed by the hydrolysis of the amide to the corresponding acid in isolated form, and esterification of the resulting acid with methanol to give methylphenidate.

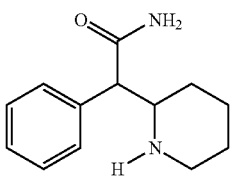 [SMILES: NC(=O)C(c1ccccc1)C1CCCCN1]

Mixture of threo and erythro isomer of amide

Patrick, K. S., *J. Med. Chem.* 24:1237-1240 (1981), discloses the process, according to disclosure, erythro- and threo-dl-2-(4-methoxyphenyl)-2-(2'-pyridyl) acetamide hydrochloride is dissolved in glacial acetic acid and $PtO_2$ is added into it. Thus, conversion from pyridine to piperidine ring takes place in hydrogen pressure. After evaporation the obtained oil is dissolved in methanol, treated with Norite and filtered and then excess of diethyl ether-HCl is added. The solvent is evaporated to obtain erythro- and threo-dl-2-(4-methoxyphenyl)-2-(2'-piperidyl)acetamide hydrochloride in 72% yield. Further it is treated with hydrochloric acid to obtain erythro- and threo-dl-2-(4-methoxyphenyl)-2-(2'-piperidyl)acetic acid hydrochloride. Alternatively, erythro- and threo-dl-2-(4-methoxyphenyl)-2-(2'-piperidyl)acetamide hydrochloride is treated with 50% potassium hydroxide for 4 days until an aliquot contained no more than 5% erythro isomer. The mixture is cooled and crystallized by ethyl acetate to give 95+% threo isomer and 53% yield. Then it is followed by treatment of 48% hydrobromic acid to obtain hydrobromide salt of corresponding threo-dl-2-(4-hydroxyphenyl)-2-(2'-piperidyl) acetic acid having 95+% threo isomer and 94% yield. The obtained white crystals are treated with methanol-HCl followed by evaporation of solvent and recrystallized with acetone-diethyl ether to get methylphenidate hydrochloride having 73% yield. The overall yield is just around 26% from erythro- and threo-dl-2-(4-methoxyphenyl)-2-(2'-pyridyl) acetamide hydrochloride, which is industrially not advantageous.

Synthetic methods for preparing racemic mixtures of threo- and erythro-α-phenyl-2-piperidineacetamides as raw materials for the preparation of threo-methylphenidate are described in U.S. Pat. Nos. 2,507,631; 2,838,519; 2,957,880 and 5,936,091; and in *J. Med. Chem.*, 39, 1201-1209 (1996). These methods disclose reduction of the pyridine ring to a piperidine ring by hydrogenation on $PtO_2$ Pt/C catalyst in glacial acetic acid as a solvent. The reaction takes about 26 hours for the completion.

Scheme 1:

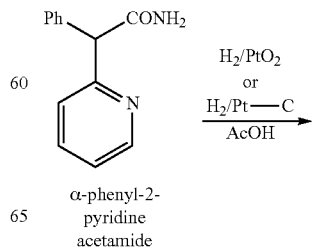

α-phenyl-2-pyridine acetamide

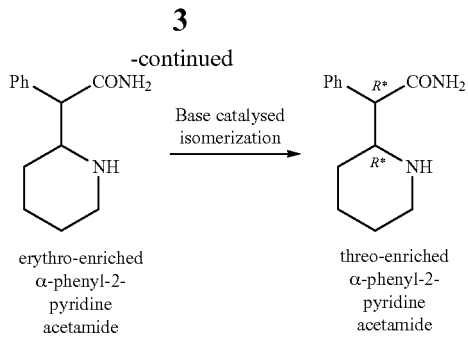

erythro-enriched α-phenyl-2-pyridine acetamide → threo-enriched α-phenyl-2-pyridine acetamide (Base catalysed isomerization)

U.S. Pat. No. 7,459,467 describes the preparation of α-phenyl-α-piperidyl-2-acetamide by treating α-phenyl-α-pyridyl-2-acetamide with 0.1N perchloric acid in acetic acid, Pd/C and alcohol as reaction media under 12-15 Kg/cm$^2$ hydrogen pressure at 45-50° C. for 15-18 hours. The catalyst is removed by filtration. The filtrate is concentrated under reduced pressure followed by basifying with aqueous sodium hydroxide solution to precipitate α-phenyl-α-piperidyl-2-acetamide. The patent is silent or not disclosing the conversion of α-phenyl-α-piperidyl-2-acetamide to methylphenidate hydrochloride. The patent discloses preparation of methylphenidate free base from α-phenyl-α-pyridyl-2-methyl acetate by using same reaction condition, reagents and solvent for the reduction as mentioned above. The preparation of methylphenidate hydrochloride from methylphenidate obtained in 78%; hence 22% yield loss is uneconomic and isolation of methylphenidate and then converson to corresponding hydrochloride salt adds more unit operations and yield loss as well. The above process for the preparation of α-phenyl-α-piperidyl-2-acetamide is not feasible at large scale because it uses 0.1N perchloric acid which is unsafe, process needs hastelloy autoclave and also has the high pressure 12-15 Kg/cm$^2$ which is not safe at large volume in autoclave. The process involves tedious and lengthy operation for isolation of α-phenyl-α-piperidyl-2-acetamide. Volumes of solvents are also 11-15 times of input; hence the process is also not environment friendly.

U.S. Pat. No. 7,229,557 describes the esterification of dl-ritalinic acid in about 20 molar equivalents of methanol saturated with hydrogen chloride gas under reflux. From the reaction, dl-threo methylphenidate hydrochloride was obtained in 37%yield.

U.S. Patent Application 2010/0179327 describes the preparation of amino acid esters such as methylphenidate. The application describes the reaction of threo-α-phenyl-α-(2-piperidinyl)acetic acid [threo 99.51%: erythro 0.49%], methanolic HCl, and trimethyl orthoacetate with heating at reflux to form methylphenidate in 69.8% yield. As per the disclosure, 69.8% yield of methylphenidate is not viable from the industrial point view, even after taking 99.51% pure threo-α-phenyl-α-(2-piperidinyl)acetic acid.

PCT application no. 2011/067783 discloses process for the preparation of methylphenidate hydrochloride by reacting α-phenyl-α-piperidyl acetamide with 20% aqueous hydrochloric acid solution and reflux for 2-6 hours. The reaction mixture is cooled and diluted by water to get clear solution followed by extracting with dichloromethane. The layers are separated and pH of aqueous layer is adjusted by adding sodium hydroxide to get threo α-phenyl-α-piperidyl-2-acetic acid in 88.6% yield having isomeric purity [threo 99.9%: erythro 0.1%]. It means the process using very pure α-phenyl-α-piperidyl acetamide to prepare pure threo α-phenyl-α-piperidyl-2-acetic acid. Thus obtained corresponding acid is converted to methylphenidate hydrochloride by treating with thionyl chloride and methanol at temperature below 10° C. The reaction mixture is kept under stirring over night at room temperature followed by distillation of methanol under reduced pressure and then cooled to 10° C. Water and ethyl acetate is added into the residue under constant stirring. The pH is adjusted by using dilute caustic solution and the layers are separated. The solvent is distilled off and treated with IPA-HCl to give methylphenidate hydrochloride.

PCT application no. 2012/080834 discloses the process for preparing methylphenidate hydrochloride by treating dl-threo ritalinic acid which may be very pure material, with HCl gas in methanol. The reaction mixture is maintained for 20 hours at 41-42° C. Trimethyl orthoformate is added into the reaction mixture in one portion, maintained for 3.5 hours at 41-42° C. and 19 hours at room temperature. The reaction mixture is distilled off and isopropanol is added simultaneously. Subsequently the reaction mixture is cooled to 2° C. for 30 minutes to get methylphenidate hydrochloride. The reagent trimethyl orthophosphate is showing hazards like acute toxicity (oral, dermal, inhalation), skin irritation, eye irritation, skin sensitization and flammable as well. Moreover that use of additional regent like trimethyl orthophosphate in high quantity i.e 2 mole equivalents for the esterification will increase the cost of the product and hazardous for the environment as well as humans. The major negative point of trimethyl orthophosphate is effluent problem; hence it is not preferable for large scale.

A major drawback of the processes described in above documents is that they all use costly catalyst such as platinum metal adsorbed on carbon or platinum oxide with a very high loading [high loading means higher amounts with respect to the starting compound (II)] for the selective reduction of pyridine ring. Platinum catalysts are known for their high catalytic activity in comparison with milder metal catalyst such as Nickel or Palladium. The order of catalytic activity is Rh>Pt>Pd>Ni. By using Pt or its oxide and Rh catalyst for hydrogenation makes the process uneconomical. Other prior art process involves reduction of pyridine ring by using palladium catalyst with harsh and hazardous reagents, additional solvents, high pressure, lengthy and high cost equipments required, which cumulatively makes the process unattractive for industrial scale.

A need exists for a more efficient and economical process for the reduction of the pyridine ring and novel approach to prepare methylphenidate hydrochloride in good yield and high purity at industrial scale.

Thus, present invention fulfills the need of the art and provides an improved and industrially applicable process for reduction of pyridine ring of amide intermediate and/or the preparation of methylphenidate hydrochloride, which provides methylphenidate hydrochloride in high purity, overall good yield and one pot synthesis of methylphenidate hydrochloride from threo-2-phenyl-2-(piperidin-2-yl) acetamide [threo NLT 85%: erythro ~12%]. The present invention can be described, as shown in scheme 2.

Scheme 2:

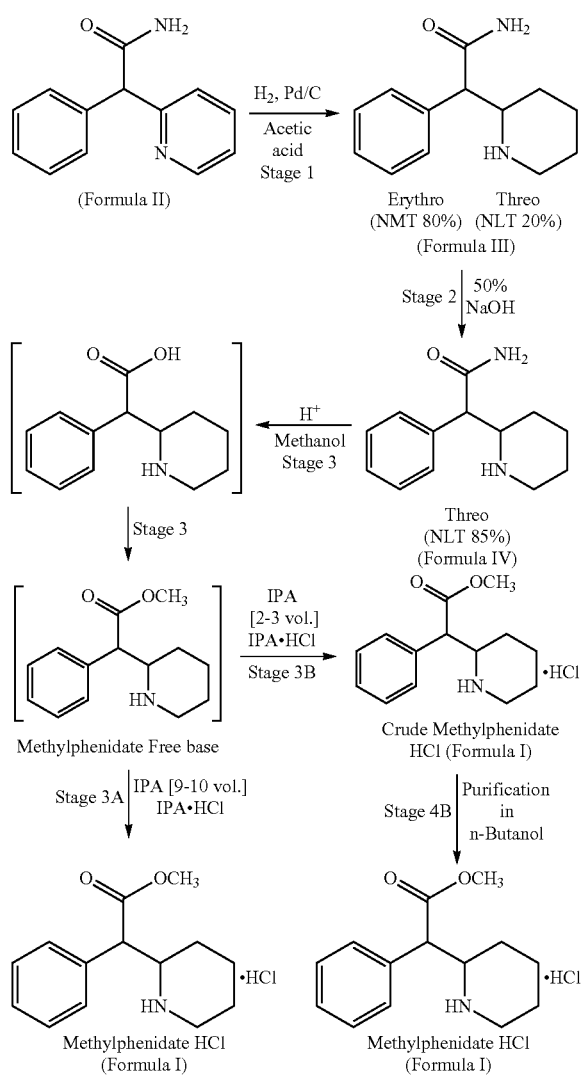

OBJECTIVE OF THE INVENTION

The principal objective of the present invention is to provide an efficient and industrially advantageous process for preparation of methylphenidate hydrochloride.

Another prime objective of the invention is to provide a process for the preparation of methylphenidate hydrochloride in single step.

Another leading objective of the invention is to provide an efficient, improved and industrially advantageous process for preparation of methylphenidate hydrochloride which is conveniently applicable to industrial scale and avoiding use of various solvents and operations.

Further one more objective of the present invention is to provide a novel process for the preparation of mixture of erythro- and threo-2-phenyl-2-(piperidin-2-yl) acetamide.

Yet additional objective of the present invention is to provide a novel one-pot process for the preparation of methylphenidate hydrochloride from threo-2-phenyl-2-(piperidin-2-yl) acetamide [threo NLT 85%: erythro ~12%].

Yet foremost objective of the present invention is to provide a process for the preparation of methylphenidate hydrochloride having high purity and good yield.

SUMMARY OF THE INVENTION

Accordingly, the present invention provides a novel process for the preparation of mixture of erythro- and threo-2-Phenyl-2-(piperidin-2-yl)acetamide of compound of formula III, process comprises the step of: treating the compound of formula II with reducing agent in acid, except any other solvent to provide a compound of formula III.

Accordingly, the present invention provides a novel one-pot process for the preparation of methylphenidate hydrochloride of formula I from threo 2-phenyl-2-(piperidin-2-yl) acetamide of formula IV, process comprises the step of: treating compound of formula IV with methanol, in the presence of catalyst and alcoholic hydrochloric acid to form compound of formula I.

Accordingly, the present invention provides a process for the preparation of methylphenidate hydrochloride of formula I.

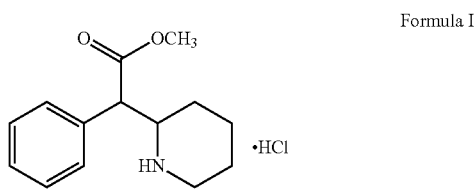 [SMILES: COC(=O)C(c1ccccc1)C1CCCCN1 ; Cl]

Formula I which proves to be efficient and industrially viable. The process comprises the steps of:

a). treating the compound of formula II,

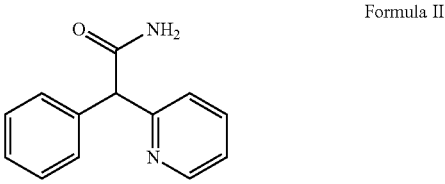 [SMILES: NC(=O)C(c1ccccc1)c1ccccn1]

Formula II with reducing agent in acid to provide a compound of formula III;

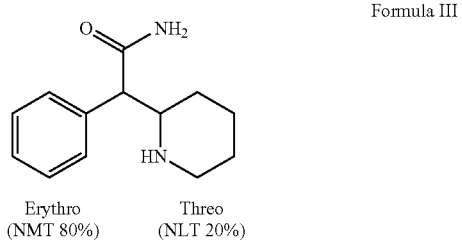 [SMILES: NC(=O)C(c1ccccc1)C1CCCCN1]

Formula III b). treating compound of formula III with an inorganic base to provide compound of formula IV;

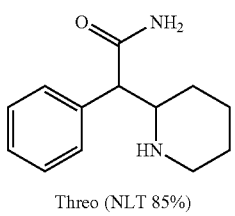

Threo (NLT 85%)

c). treating compound of formula IV with methanol, in the presence of catalyst and alcoholic hydrochloric acid to provide compound of formula I; and)

d). optionally purifying compound of formula I by treating with suitable solvent.

Accordingly, the present invention provides a process for the purification of methylphenidate hydrochloride of formula I in alcohol.

Accordingly, the present invention provides an improved process for the preparation of pharmacopoeial grade methylphenidate hydrochloride.

DETAILED DESCRIPTION OF THE INVENTION

All ranges recited herein include the endpoints, including those that recite a range "between" two values. Terms such as "about", "generally" and the like are to be construed as modifying a term or value such that it is not an absolute. Such terms will be defined by the circumstances and the terms that they modify as those terms are understood by those skill in the art. This includes, at very least, the degree of expected experimental error, technique error and instrument error for a given technique used to measure a value.

The term "NLT" means "not less than" and "NMT" means "not more than" with respect to purity of the compound.

The present invention provides an improved and efficient process for the preparation of methylphenidate hydrochloride of formula I.

According to the embodiment of the invention provides an industrially viable process for preparation of methylphenidate hydrochloride starting from compound of formula II.

Stage 1:

The preferred embodiment of the present invention is to provide a process to prepare compound of formula III from compound of formula II. The compound of formula II can be reduced in the presence of reducing agent to form compound of formula III. Generally the reaction involves hydrogenation of compound of formula II in the presence of reducing agent in a solvent at a particular temperature for sufficient time. Reducing agents include palladium on carbon. Solvent includes acid solvent, preferably glacial acetic acid or aqueous acetic acid and the like, except any other solvent. The reaction mixture is heated at 50-70° C. for 1 to 24 hours, preferably at 55-65° C. for about 15 hours under pressure about 4-5 Kg/cm$^2$. After completion of the reaction, the mixture is filtered and followed by workup procedure to obtain compound of formula III.

More precisely, the workup can be done by concentrating the filtrate under vacuum below 80° C. followed by addition of water and treated with activated carbon to decolorize the material. Then after pH can be adjusted using a base. Preferably the pH can be 10-12, more preferably near about 12. The suitable base can be selected from the group comprising of inorganic base. Inorganic base include alkali or alkaline metal hydroxides, carbonates, bicarbonates, alkoxides; wherein inorganic base is preferably sodium hydroxide, potassium hydroxide, lithium hydroxide, sodium carbonate, potassium carbonate, lithium carbonate, sodium bicarbonate, potassium bicarbonate, lithium bicarbonate; wherein inorganic base is more preferably sodium hydroxide. The base treatment results in precipitation of free base of formula III.

The principle advantages of this particular stage are the process does not involve costly catalyst like platinum or rhodium catalyst for the reduction. Moreover that the process involves use of acid itself as a solvent and no additional solvents are required; hence the recovery of acid by the distillation and good yield of the product makes the process economical or cost-effective. The recovered acid is achieved in good quality which can be used further without additional purification. In addition, the process become environment friendly because of less effluent and negligible effluent treatment cost. In this way the present invention is ameliorating the major drawbacks of the prior art processes.

Stage 2:

The compound of formula III can be treated with base to get pure compound of formula IV. The racemic mixture of formula III upon treatment with inorganic base resulted in major threo isomer of formula IV. The inorganic base include alkali or alkaline metal hydroxides, carbonates, bicarbonates, alkoxides; wherein inorganic base is preferably sodium hydroxide, potassium hydroxide, lithium hydroxide, sodium carbonate, potassium carbonate, lithium carbonate, sodium bicarbonate, potassium bicarbonate, lithium bicarbonate; wherein inorganic base is more preferably sodium hydroxide, more preferably 50% aqueous sodium hydroxide. The reaction mixture is heated 80-130° C. for about 5-10 hours, preferably at 100-110° C. for about 8 hours. After completion of the reaction, the reaction mixture is cooled to 0-15° C., preferably at 10-15° C. to isolate the pure compound of formula IV having major threo isomer NLT 85%.

The present invention delivers more pure compound of formula IV as the process parameters are set in the way which gives the good yield and purity as well.

Stage 3A:

The preferred embodiment of the present invention is to provide a novel one-pot process to prepare methylphenidate hydrochloride of formula I from compound of formula IV. The esterification can be performed by reacting formula IV with methanol in the presence of catalyst. The catalyst can be selected from sulfuric acid, hydrochloric acid or acetic acid and the like. Then after, in-situ generated methylphenidate free base is converted to corresponding hydrochloride salt by reacting with alcoholic hydrochloric acid.

More specifically, Compound of formula IV is treated with methanol at 25-30° C. temperature followed by cooling. The cooling temperature can be −5-10° C., preferably 0-5° C. The catalyst is added to the reaction mixture and stirred for a while at 10-15° C. and the temperature is raised to distill the methanol partially. Preferably the temperature can be raised up to reflux temperature. Further, according to batch size fresh methanol is added into the reaction mixture and further maintained at reflux temperature for sufficient time. Preferably the reaction is maintained 5-50 hours, more preferably 25-30 hours. After completion of distillation the thick slurry mass is cooled to 20-25° C. and water is added followed by further cooling at temperature 10-15° C. and stirred for 10-15 minutes. The pH is adjusted at 6-8 by using base. The base can be sodium hydroxide, potassium hydroxide, lithium hydroxide, sodium carbonate, potassium carbonate, lithium carbonate, sodium bicarbonate, potassium bicarbonate, lithium bicarbonate or ammonia, preferably sodium hydroxide. The suitable solvent is added into the reaction mixture at temperature about 25-30° C. The solvent include dichloromethane, ethylaceate diethylether, diisopropylether, methylethylether, toluene or xylene or mixture thereof. Further pH is adjusted to 11.5-12.5 and the mixture is stirred for 30 minutes. The organic layer is separated and solvent is distilled out. After completion of distillation, suitable solvent is added into the oily mass (in-situ venerated methylphenidate free base) followed by charcoal treatment. The suitable solvent can be selected from methanol, ethanol, n-propanol, isopropanol, n-butanol, isobutanol, tert-butanol or acetone and mixture thereof. The volume of the solvent used against formula IV can be 1-20 volumes, preferably 9-10 volumes. The reaction mixture is filtered and filtrate is cooled to 5-10° C. Alcoholic hydrochloric acid is added into the reaction mixture and stirred for a while at 5-10° C. An alcoholic hydrochloric acid, wherein alcohol can be selected from methanol, ethanol, isopropanol, n-butanol, isobutanol, tert-butanol and the like. The reaction mixture is heated at 40-120° C., preferably 50-55° C. for 10-15 minutes and subsequently cooled to 5-10° C. The reaction mixture is then maintained for 30 minutes, filtered, washed and dried to get more than 99.7% pure methylphenidate hydrochloride of formula I.

The main advantage of this stage is to provide the product via one-pot synthesis. A one-pot synthesis is a strategy to improve the efficiency of a chemical reaction whereby a reactant is subjected to successive chemical reactions in just one reactor. This is much desired by chemists because avoiding a lengthy separation process, purification of the intermediate compounds and avoid drying step would save time and resources while increasing yield. The greatest advantage of this method is that fewer synthetic and isolation steps are employed as compared to the multi-step approach reported into the prior art.

Stage 3B:

As per the observations of scientists of the present invention is that the use of 9-10 volumes of the solvent gives higher quality as compared to use of 2-3 volumes of solvent at particular stage. The difference is broadly described as shown in below table.

The volumes of solvent (i.e methanol, ethanol, n-propanol, isopropanol, n-butanol, isobutanol, tert-butanol or acetone and mixture thereof) added into oily mass of methylphenidate free base obtained from stage 3A, are preferably 2-3 volumes.

In other words, after distillation of the solvent (i.e dichloromethane, ethylaceate diethylether, diisopropylether, methylethylether, toluene or xylene or mixture thereof) described in stage 3A, the obtained oily mass of methylphenidate free base is treated with different solvent volumes and gives different purity results as described in below table. Hence stage 3B may need purification to remove unwanted isomer and impurities.

|  | Stage 3A | Stage 3B |
| --- | --- | --- |
| Solvent | Isopropanol | Isopropanol |
| Solvent Volume | 9-10 | 2-3 |
| HPLC Purity | ~99.8% | ~99.3% |

Stage 4B:

Methylphenidate hydrochloride of formula I from stage—3B is purified by treating with suitable solvent. The suitable solvent includes methanol, ethanol, isopropanol, n-butanol, isobutanol, tert-butanol, acetone, acetonitrile or mixture thereof. The reaction temperature is ambient to reflux temperature, preferably up to 110-120° C. for a time sufficient. The reaction mixture is then cooled to 0-30° C., preferably 25-30° C. and maintained for 30 minutes followed by filtration at 25-30° C. The obtained cake is washed with solvent, dried to give more than 99.8% pure methylphenidate hydrochloride.

Hence the parameters set for the purification in present invention make the product pharmacopoeially acceptable worldwide.

The invention is further defined by reference to the following examples describing in detail by the preparation of the compounds of the invention. It will be apparent to those skilled in the art that many modifications, both to materials and methods, may be practiced without departing from the scope of the invention.

EXAMPLES

Stage—1: Preparation of 2-phenyl2-(piperidin-2-yl)acetamide

A solution of 2-phenyl-2-(pyridine2-yl) acetamide (200 g, 0.942 mole) it glacial acetic acid (1000 ml) was hydrogenated in the presence of palladium on carbon (20 gm) at 55-65° C. under 4.5 Kg/cm$^2$ of hydrogen for 15 hours. The reaction mixture was filtered through celite bed. The obtained filtrate was concentrated under vacuum below 80° C. and residue were dissolved in water (1400 ml) and treated with activated carbon. The reaction mixture filtered through celite bed. The pH 12 was adjusted with aqueous sodium hydroxide. The precipitated free base was washed with water and the product dried in tray dryer at 70° C. to give 180 g of product of racemic mixture of erythro- and threo-2-phenyl-2-(piperidine-2-yl) acetamide as a white solid having HPLC purity: Erythro content: NMT 80% Threo content: NLT 20%.

Stage—2: Preparation of threo-2-phenyl-2-(piperidin-2-yl) acetamide

Racemic mixture of erythro- and threo-2-phenyl-2-(piperidine-2-yl) acetamide (100 gm) was treated with 50% aqueous sodium hydroxide (600 gm). The reaction mixture was heated at 100-110° C. for 8 hours under stirring followed by cooling at 10-15° C. The obtained material was filtered and wet cake was given water (300 ml×3) slurry. Dried the cake at 60-70° C. to give 90 gm titled compound having HPLC purity: Threo content: NLT 85%, Erythro content: NMT 15%.

Stage—3A [Method 1]: Preparation of Methylphenidate Hydrochloride from threo-2-phenyl-2-piperidyl acetamide [Threo isomer NLT 85%]

In methanol (800 ml), threo-2-phenyl-2-(piperidin-2-yl) acetamide (200 gm) was added at ambient temperature. The reaction mixture was cooled to 0-5° C. followed by addition of sulfuric acid (359 gm) drop wise within 45-60 minutes. The mass was stirred for 10-15 minutes at 10-15° C. and temperature was then raised up to 25-30° C. The reaction mass was heated at temperature 75-80° C. within 45-60 minutes and maintained at reflux for 20 hours to distill 2 volume of methanol. Fresh 2 volume of methanol was added into the reaction mass. Further it is maintained at reflux for 8 hours. After completion of reaction, methanol was distilled out at 75-80° C. and degassed under vacuum. The thick residue was cooled to 20-25° C. and water (2800 ml) was added. Cooled the mass up to 10-15° C. and stirred for 10 minutes followed by adjusting pH at 6-8 by adding caustic soda. Into the reaction mixture dichloromethane (600 ml) was added at 25-30° C. and pH was adjusted to 11.5-12.5. The mixture was then stirred for 30 minutes at 25-30° C. The organic layer was separated. Again dichloromethane (200ml×2) was added to aqueous layer and separated. Combined the organic layers. Dichloromethane is distilled out at temperature 45-50° C. and degassed under vacuum. After completion of distillation, isopropanol (2000 ml) added into the oily mass followed by charcoal treatment. The reaction mixture was filtered and washed with isopropanol (200 ml). The filtrate was then cooled up to 5-10° C. Isopropanolic hydrochloric acid (190 gm) was added to the reaction mass followed by stirring for 30 minutes at 5-10° C. The reaction mixture was heated at 50-55° C. for 10-15 minutes followed by cooling at 5-10° C. The reaction mass was maintained at 5-10° C. for 30 minutes. Filtered the mass at 5-10° C. and washed with isopropanol (200 ml). The wet cake was dried at 70-75° C. to get methylphenidate hydrochloride (170 gm) having HPLC purity: Threo content: 99.8%, Erythro content: 0.1%.

Stage—3B [Method 2]: Preparation of Methylphenidate Hydrochloride from threo-2-phenyl-2-piperidyl acetamide [Threo isomer NLT 85%]

In methanol (800 ml), threo-2-phenyl-2-(piperidin-2-yl) acetamide (200 gm) was added at ambient temperature. The reaction mixture was cooled to 0-5° C. followed by addition of sulfuric acid (359 gm) drop wise within 45-60 minutes. The mass was stirred for 10-15 minutes at 10-15° C. and temperature was then raised up to 25-30° C. The reaction mass was heated at temperature 75-80° C. Within 45-60 minutes and maintained at reflux for 20 hours to distill 2 volume of methanol. Fresh 2 volume of methanol was added into the reaction mass. Further it is maintained at reflux for 8 hours. After completion of reaction, methanol was distilled out at 75-80° C. and degassed under vacuum. The thick residue was cooled to 20-25° C. and water (2800 ml) was added. Cooled the mass up to 10-15° C. and stirred for 10 minutes followed by adjusting pH at 6-8 by adding caustic soda. Into the reaction mixture dichloromethane (600 ml) was added at 25-30° C. and pH was adjusted to 11.5-12.5. The mixture was then stirred for 30 minutes at 25-30° C. The organic layer was separated. Again dichloromethane (200ml×2) was added to aqueous layer and separated. Combined the organic layers. Dichloromethane is distilled out at temperature 45-50° C. and degassed under vacuum. After completion of distillation, isopropanol (400 ml) was added to the reaction mass followed by charcoal treatment. Filtered the reaction mass, cooled up to 5-10° C. and isopropanolic hydrochloric acid (190 gm) was added into it. Stirred the mass for 30 minutes at 5-10° C. The reaction mass was heated at 50-55° C. and maintained for 10-15 minutes followed by cooling at 5-10° C. The reaction mass was maintained at 5-10° C. for 1 hour. Filtered the mass at 5-10° C. and washed with isopropanol (200 ml). The wet cake was dried at 70-75° C. to get crude 190 gm methylphenidate hydrochloride having HPLC purity: Threo content: 99.32% Erythro content: 0.5%.

Stage—4B: Purification of crude Methylphenidate hydrochloride

Crude Methylphenidate hydrochloride (190 gm) from stage—3B [Method 2] was added into the n-butanol (874 ml) at temperature 25-30° C. The reaction mass was heated up to 110-120° C. and maintained for 10-15 minutes. The mass was then cooled to 25-30° C. within 2-3 hours and maintained for 30 minutes followed by filtration at 25-30° C. The obtained cake was washed with n-butanol (190 ml) and dried at 75-80° C. under vacuum to get pure 168 gm pure methylphenidate hydrochloride having HPLC purity: Threo content: 99.90%, Erythro content: 0.05%.

The invention claimed is:
1. A process for preparation of methylphenidate hydrochloride of formula I, comprising the steps of:
   a). treating racemic 2-phenyl-2-(pyridine-2 -yl) of formula II with palladium on carbon in acetic acid to provide a racemic mixture of erythro- and threo-2-Phenyl-2-(piperidin-2-yl)acetamid of formula III, wherein the racemic mixture comprises erythro content that is not more than 80% and threo content that is not less than 20%, and wherein the formula II is:

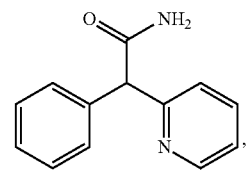

and
wherein the formula III is:

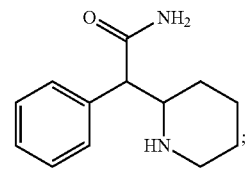 [SMILES: NC(=O)C(c1ccccc1)C1CCCCN1]

b). treating the racemic mixture of erythro- and threo-2-Phenyl-2-(piperidin-2-yl) acetamide of formula III with an inorganic base to provide at least 85% threo 2-phenyl-2-(piperidin-2-yl) acetamide and at most 15% erythro-2-phenyl-2-(piperidin-2-yl) acetamide of formula IV; and
   c). treating the at least 85% threo-2-phenyl-2-(piperidin-2-yl) acetamide of formula IV which contains up to 15% erythro-2-phenyl-2-(piperidin-2-yl) acetamide with methanol, in the presence of catalyst followed by adding, alcoholic hydrochloric acid to provide compound of formula I having at least 99% threo content, wherein in the preparation of methylphenidate hydrochloride of formula I from threo 2-phenyl-2-(piperidin-2-yl) acetamide of formula IV, the threo 2-phenyl-2-(piperidin-2-yl) acetamide of formula IV is subjected to successive chemical reactions in one reactor, wherein the formula IV is:

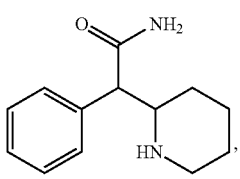 [SMILES: NC(=O)C(c1ccccc1)C1CCCCN1]

and
wherein the formula I is:

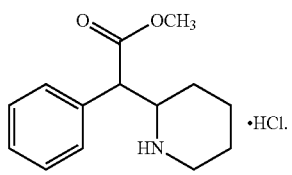 [SMILES: COC(=O)C(c1ccccc1)C1CCCCN1]

2. The process according to claim 1, wherein the catalyst is selected from the group consisting of sulfuric acid, hydrochloric acid, acetic acid or mixture thereof.

3. The process according to claim 1, wherein the alcohol is selected from the group consisting of methanol, ethanol, isopropanol, n-butanol, isobutanol, tert-butanol.

4. The process according to claim 1, wherein the step a) is performed under hydrogen pressure at about 4.5 kg/cm$^2$; and in step b), said inorganic base is selected from the group consisting of alkali or alkaline metal hydroxides, carbonates, bicarbonates, and alkoxides.

5. The process according to claim 1, wherein the acetic acid is used in 5 volumes.

6. The process according to claim 1, wherein the inorganic base is selected from the group consisting of sodium hydroxide, potassium hydroxide, lithium hydroxide, sodium carbonate, potassium carbonate, lithium carbonate, sodium bicarbonate, potassium bicarbonate, and lithium bicarbonate.

* * * * *